(12) United States Patent
Jankowski et al.

(10) Patent No.: US 9,682,181 B2
(45) Date of Patent: Jun. 20, 2017

(54) DEVICE AND METHOD FOR REMOVING PROTEIN-BOUND TOXINS FROM THE BLOOD OF PATIENTS USING A HIGH-FREQUENCY, ELECTROMAGNETIC FIELD AND AN ELECTROSTATIC DIRECT CURRENT FIELD

(71) Applicant: FRESENIUS MEDICAL CARE DEUTSCHLAND GMBH, Bad Homburg (DE)

(72) Inventors: Joachim Jankowski, Stahnsdorf (DE); Anselm Fabig, Zeuthen (DE); Ulrich Tschulena, Frankfurt (DE); Carsten Müller, Euerbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 7 days.

(21) Appl. No.: 14/759,154

(22) PCT Filed: Jan. 6, 2014

(86) PCT No.: PCT/EP2014/050080
§ 371 (c)(1),
(2) Date: Jul. 2, 2015

(87) PCT Pub. No.: WO2014/106654
PCT Pub. Date: Jul. 10, 2014

(65) Prior Publication Data
US 2015/0335811 A1 Nov. 26, 2015

(30) Foreign Application Priority Data

Jan. 4, 2013 (DE) .................. 10 2013 100 050

(51) Int. Cl.
*C02F 1/48* (2006.01)
*A61M 1/16* (2006.01)
(Continued)

(52) U.S. Cl.
CPC ............ *A61M 1/16* (2013.01); *A61M 1/3681* (2013.01); *B01D 61/30* (2013.01); *B01D 61/32* (2013.01);
(Continued)

(58) Field of Classification Search
CPC ........ A61M 1/14; A61M 1/3681; A61M 1/16; A61M 1/1601; A61M 1/3618;
(Continued)

(56) References Cited

U.S. PATENT DOCUMENTS 5,261,874 A * 11/1993 Castle ................ A61B 5/14557
604/28
7,935,906 B2 * 5/2011 Kibar ........................ B03C 1/24
209/127.1
(Continued)

FOREIGN PATENT DOCUMENTS

CN 1551795 A 12/2004
DE 27 31 744 A1 2/1979
(Continued)

OTHER PUBLICATIONS

EPO Office action dated May 19, 2016, for corresponding European Patent application 14702194.3, (5 pages).
(Continued)

*Primary Examiner* — Nam Nguyen
*Assistant Examiner* — Julia Wun
(74) *Attorney, Agent, or Firm* — Lewis Roca Rothgerber Christie LLP

(57) ABSTRACT

A dialysis device including a dialysis circuit, a blood circuit; and a dialyzer. The dialysis device includes a device for generating a high-frequency electromagnetic field and a device for generating an electrostatic direct current field. Both devices are designed and arranged in such a way that blood to be treated can be exposed to the high-frequency
(Continued)

electromagnetic field and the electrostatic direct current field when passing through the dialyzer.

17 Claims, 6 Drawing Sheets

(51) Int. Cl.
*B01D 61/42* (2006.01)
*B01D 61/32* (2006.01)
*B01D 61/30* (2006.01)
*A61M 1/36* (2006.01)

(52) U.S. Cl.
CPC .............. *B01D 61/422* (2013.01); *C02F 1/48* (2013.01); *A61M 2202/0445* (2013.01); *A61M 2202/07* (2013.01); *A61M 2205/054* (2013.01); *A61M 2205/057* (2013.01); *B01D 2311/2603* (2013.01); *B01D 2311/2615* (2013.01); *B01D 2313/365* (2013.01); *C02F 2201/48* (2013.01)

(58) Field of Classification Search
CPC .. A61M 1/3621; A61M 1/3653; A61M 1/367; A61M 2205/0272; C02F 1/48; C02F 1/487; C02F 2201/48
USPC .............................. 210/223, 222, 167.29, 695
See application file for complete search history.

(56) References Cited

U.S. PATENT DOCUMENTS

| | | | | |
|---|---|---|---|---|
| 2003/0153024 A1* | 8/2003 | Sullivan | ........... | G01N 35/00594 435/7.92 |
| 2003/0187380 A1 | 10/2003 | Botto et al. | | |
| 2005/0015040 A1 | 1/2005 | Wuepper | | |
| 2005/0082225 A1 | 4/2005 | Kreymann | | |
| 2009/0012655 A1* | 1/2009 | Kienman | ................ | A61M 1/28 700/300 |
| 2009/0120876 A1 | 5/2009 | Kreymann | | |
| 2015/0306298 A1 | 10/2015 | Tschulena et al. | | |
| 2015/0343134 A1 | 12/2015 | Tschulena et al. | | |

FOREIGN PATENT DOCUMENTS

| | | |
|---|---|---|
| DE | 196 51 355 A1 | 6/1998 |
| DE | 10 2008 050 849 A1 | 4/2010 |
| DE | 10 2009 011 901 A1 | 9/2010 |
| DE | 10 2011 078 695 A1 | 1/2013 |
| DE | 10 2013 100 050 A1 | 7/2014 |
| EP | 1 362 605 A1 | 11/2003 |
| EP | 1 523 350 B1 | 4/2005 |
| FR | 2 087 416 | 12/1971 |
| RO | 122077 B1 | 12/2008 |
| WO | WO 03/020403 A1 | 3/2003 |
| WO | WO 2014/095072 A1 | 6/2014 |
| WO | WO 2014/095073 A1 | 6/2014 |

OTHER PUBLICATIONS

International Search Report and Written Opinion of corresponding PCT/EP2014/050080, dated Apr. 15, 2014, 12 pages.
Machine translation of German Search Report for Application No. DE 10 2013 100 050.9, dated Sep. 18, 2013, 8 pages.
Office Action, with English translation, dated Jul. 29, 2016, for corresponding Chinese Patent Application No. 201480003876.X (13 pages).

\* cited by examiner

DEVICE AND METHOD FOR REMOVING PROTEIN-BOUND TOXINS FROM THE BLOOD OF PATIENTS USING A HIGH-FREQUENCY, ELECTROMAGNETIC FIELD AND AN ELECTROSTATIC DIRECT CURRENT FIELD

CROSS-REFERENCE TO RELATED APPLICATION(S)

This application is a National Phase Patent Application and claims priority to and the benefit of International Application Number PCT/EP2014/050080, filed on Jan. 6, 2014, which claims priority to German Patent Application Number 10 2013 100 050.9, filed on Jan. 4, 2013, the entire contents of all of which are incorporated herein by reference.

The primary function of the kidneys is to excrete substances which are normally eliminated with the urine, the so-called uremic toxins. The kidneys of patients suffering from chronic renal failure are no longer able to fulfil this function, which, if untreated, results in poisoning and death of the patient within a short time. Dialysis is the instrument of choice used to alleviate the acute and chronic disease and to bridge the gap until a suitable donor organ is available. Dialysis is based on the principle of an exchange of substances by means of filtration or diffusion. The membranes used at present act as mere filtration and/or diffusion membranes, ensuring that substances up to a defined maximum size are removed from the blood to be treated. However, the methods of dialysis used at present do not, as a rule, achieve a complete separation of uremic toxins, since part of the substances which are normally eliminated with the urine are bound to proteins. These are, among others, low-molecular aromatic substances. Uremic toxins which, as a rule, can be bound to proteins include, for example, phenylacetic acid, p-hydroxyhippuric acid and indoxyl sulfate. As a result, the relevant substances accumulate in the organism of the patient and cause secondary diseases of acute and chronic renal failure. As a result, patients suffering from chronic renal failure increasingly develop secondary diseases, such as cardiovascular disease, leading to an increased mortality rate.

Aromatic, hydrophobic uremic toxins have a low solubility in water. This brings about adsorptive effects between these substances and plasma proteins in most cases. Said adsorptive effects are caused by various types of interaction. These include, above all, hydrogen bridge bonds, ionic bonding and dipole-dipole interaction (van der Weals forces). If the substances which are normally eliminated with the urine are bound to plasma proteins, such as albumin, their effective molecular weight can increase. The resulting molecular weight of the protein-bound uremic toxins is thus generally above the exclusion limit of the dialysis membranes used, therefore preventing effective removal of said toxins during dialysis.

As a consequence, only the portion of the relevant uremic toxin that is not bound to proteins can be separated by dialysis. The protein-bound portion (up to 95% of the total amount of the uremic toxin) remains essentially unchanged. Due to the equilibrium according to the law of mass action between uremic toxins which are bound to proteins and those which are not, the initial concentrations of uremic toxins which are not bound to proteins are substantially reached again in the plasma of patients suffering from chronic renal failure immediately after dialysis. As the pathophysiological and pathochemical effects are in particular caused by uremic toxins not bound to proteins, the fact that said equilibrium is re-established initiates a fatal process for the patients. This vicious circle is the underlying cause of the numerous pathological manifestations of chronic renal failure. To date, there are no conventional methods by means of which protein-bound uremic toxins can also effectively be removed from the blood to be treated during dialysis.

The object of the present invention is to reduce or to avoid at least one drawback of the prior art described above. In particular, it is an object of the invention to provide means and ways for effectively removing protein-bound uremic toxins from the blood of dialysis patients.

The object is achieved by using a high-frequency electromagnetic field and an electrostatic direct current field in a method of dialysis where a dialyzer is used for the exchange of substances, in particular for hemodialysis or hemofiltration.

The invention is based on the finding that the bonds between uremic toxins and plasma proteins are not, as a rule, "true" chemical (covalent) bonds but reversible bonds. These bonds are substantially based on the electrostatic properties of and the interaction between the relevant molecules. It has been found that the strength of said bonds or intensity of said interactions can be reduced by applying high-frequency electromagnetic fields. If high-frequency electromagnetic fields are used during dialysis, the portion of protein-bound uremic toxins can be greatly reduced. In the context of dialysis in everyday clinical practice, the additional use of high-frequency electromagnetic fields serves to increase the percentage of protein-bound uremic toxins which are released from the protein-bound state. As a result, the relevant uremic toxins can be dialyzed to a greater extent and more effectively. The uremic toxins which are released from the protein-bound state predominantly have a positive or negative electrical charge. The introduction of a static or rotating electrostatic direct current field means that the uremic toxins released from the protein-bound state can be circulated in the dialyzer in the direction of the dialysis membrane. An increase of the diffusion pressure is therefore achieved with respect to these uremic toxins during the dialysis and the uremic toxins released from the protein-bound state are more effectively removed from the blood to be treated. In the solution according to the invention, uremic toxin is therefore initially released from its protein-bound state by the action of a high-frequency electromagnetic field and the previously released uremic toxin is circulated by the action of an electrostatic direct current field in the direction of the dialysis membrane and therefore increasingly removed from the blood to be treated. As a result, an improved removal of protein-bound uremic toxins from the blood to be treated is achieved.

The present invention relates in particular to a dialysis device. A dialysis device comprises, as a rule, a dialysis circuit, a blood circuit and a dialyzer for the exchange of substances between the blood to be treated of the blood circuit and the dialysate of the dialysis circuit. The dialysis device according to the invention is characterized in that it has means for generating a high-frequency electromagnetic field and means for generating an electrostatic direct current field, wherein both means are designed and arranged in such a way that blood to be treated can be exposed to the high-frequency electromagnetic field and the electrostatic direct current field when passing through the dialyzer.

The dialysis device according to the invention has a dialysis circuit. The dialysate which is to be used as a dialyzing fluid is circulated in the dialysis circuit. The term "dialysis circuit" means a pipe system in which the dialysate, which is first contained in a reservoir, can be moved through the dialyzer, e.g. by means of a pump, in such a manner that the dialyzing fluid is passed through the dialyzer in a direction opposite to that of the blood to be treated and on the side of the dialyzer membrane facing away from said blood. Once the dialysate has passed through the dialyzer, it can be discharged and collected in another container if appropriate. Alternatively, the dialysate can be returned to the dialysis circuit in order to pass through the dialyzer again.

The dialysis device according to the invention has a blood circuit. The blood to be treated is circulated in the blood circuit. The term "blood circuit" means a pipe system in which the blood to be treated is obtained from the patient and can be moved through the dialyzer, e.g. by means of a pump, in such a way that the blood to be treated is passed through the dialyzer in a direction opposite to that of the dialysate and on the side of the semipermeable dialyzer membrane facing away from the dialysate. Once it has passed through the dialyzer, the treated blood is returned to the patient.

A dialyzer is used for the exchange of substances in the dialysis device according to the invention. The object of said dialyzer is to remove uremic toxins as effectively as possible from the blood to be treated. In the dialyzer, the blood to be treated and a liquid that is to be used as a dialyzing fluid, the so-called dialysate, are separated from each other by a semipermeable membrane. As a rule, said dialysate flows through the dialyzer in a dialysis circuit in a direction contrary to that of the blood flowing in the blood circuit. The exchange of substances between the blood to be treated on the one side of the semipermeable membrane of the dialyzer and the dialysate on the other takes place through said membrane. The uremic toxins are transported through the membrane by diffusion or convection. The selectivity of the exchange of substances is determined by the properties of the membrane, e.g. the pore size, on the one hand, and by the composition of the dialysate on the other. Suitable dialyzers are described in the prior art, and their use is known to the person skilled in the art. Usually, capillary dialyzers are used. The dialyzer preferably comprises a semipermeable membrane having a size exclusion limit selected from the range from 10,000 to 25,000 Da, preferably from 14,000 to 17,000 Da.

The blood to be treated is exposed to a high-frequency electromagnetic field when the blood to be treated passes through the dialyzer and/or while the blood to be treated is in contact with a semipermeable membrane of the dialyzer. To this end, the dialysis device according to the invention has means for generating a high-frequency electromagnetic field.

The means for generating a high-frequency electromagnetic field can be designed and arranged in such a way that the blood to be treated can be exposed to the high-frequency electromagnetic field when the blood to be treated passes through the dialyzer and/or while the blood to be treated is in contact with a semipermeable membrane of the dialyzer. To this end, the means for generating the high-frequency electromagnetic field can be arranged in such a way that a part, a predominant part or the entire dialyzer is directly exposed to the high-frequency electromagnetic field along the axis of the direction of flow of the blood to be treated. In particular, the means for generating the high-frequency electromagnetic field can be arranged on the outer surface of the dialyzer of the dialysis device according to the invention or form an integral part of the dialyzer.

In a preferred variant the means for generating a high-frequency electromagnetic field are arranged in such a way that the blood to be treated is exposed to the high-frequency electromagnetic field as soon as it enters the dialyzer. This approach has the advantage that the uremic toxins are released from the protein-bound state as soon as the blood starts passing through the dialyzer, so that the entire capacity of the dialyzer is available for the exchange of substances with the dialysate. If the blood to be treated is exposed to the high-frequency electromagnetic field while it is in contact with the dialyzer, the blood to be treated can be exposed to the high-frequency electromagnetic field during the entire passage through the dialyzer or only during part of said passage. It is also possible for the means for generating a high-frequency electromagnetic field to be arranged in the dialysis device in such a way that the blood to be treated is exposed to a high-frequency electromagnetic field at several points during its passage through the dialyzer.

In the dialysis device according to the invention, means can be used which generate high-frequency electromagnetic fields which have a frequency from 100 kHz to 1 GHz, for example, preferably from 10 MHz to 500 MHz, particularly preferably from 80 MHz to 170 MHz, very particularly preferably from 100 MHz to 120 MHz, still more preferably from 110 MHz to 115 MHz and most especially preferably from 110 MHz to 113 MHz and from 110 MHz to 111 MHz. Alternative preferred ranges for the frequency of the high-frequency electromagnetic fields to be generated are 0.5 MHz to 100 MHz, particularly preferably 1 MHz to 50 MHz, very particularly preferably 1 MHz to 20 MHz.

The means can be designed in such a way that the blood to be treated is exposed to a high-frequency electromagnetic field whose frequency remains substantially constant over time. Alternatively, the high-frequency electromagnetic field can have a varying frequency, wherein the frequency and/or the field strength can be varied in a regular or irregular manner. In an exemplary embodiment, the blood to be treated is exposed to a high-frequency electromagnetic field whose frequency is relatively low at the beginning, for example 1 MHz, and whose frequency is increased over time until a predefined maximum frequency is reached, for example 20 MHz, or for example from 100 MHz to 170 MHz. Alternatively, the blood to be treated can also be exposed to a high-frequency electromagnetic field having a high maximum frequency at the beginning which is reduced over time until a predefined minimum frequency is reached. The use of means for generating high-frequency electromagnetic fields with varying frequencies serves to improve the effectiveness of breaking the bonds between uremic toxins and plasma proteins.

To achieve an effective elimination of the bonds between uremic toxins and plasma proteins, it is advantageous if the high-frequency electromagnetic field is applied to the blood/plasma to be treated for a defined period of time, so that atoms of the relevant molecules and/or the entire molecules can be made to oscillate. To this end, the blood to be treated can be exposed to the high-frequency electromagnetic field according to the invention for a time of at least $\frac{1}{10}$ seconds, preferably for a time of at least $\frac{1}{2}$ seconds, particularly preferably for a time of at least one second.

To separate the uremic toxins from the plasma proteins as effectively as possible, it can be advantageous to arrange means which generate high-frequency electromagnetic fields having a defined electric or magnetic field strength in the dialysis device according to the invention. Means are therefore preferably used for generating a high-frequency electromagnetic field, which has an electric field strength of ≤250 V/m, in particular from 1 to 100 V/m, preferably from 1 to 10 V/m. Means can, for example, be used for generating a high-frequency electromagnetic field which has a magnetic flux density of ≤100 mTesla, preferably from 0.001 to 100 mTesla, particularly preferably from 0.01 to 10 mTesla, in particular from 0.01 to 2 mTesla. In a particular embodiment, means are used for generating a high-frequency electromagnetic field which has a magnetic flux density of approximately 31 mTesla.

Means and methods for generating suitable high-frequency electromagnetic fields are known to the person skilled in the art such as, for example, suitable field generators. The dialysis device according to the invention can, for example, comprise a high-frequency coil, a high-frequency electrode and/or a high-frequency capacitor to generate a high-frequency electromagnetic field.

In the dialysis device according to the invention the blood to be treated can be exposed to a high-frequency electromagnetic field and an electrostatic direct current field when the blood to be treated passes through the dialyzer and/or while the blood to be treated is in contact with a semipermeable membrane of the dialyzer. To this end, the dialysis device according to the invention has means for generating an electrostatic direct current field.

An electrostatic direct current field is an electrostatic field which is constant in its alignment over time, in contrast to a periodically changing alternating current field. Electrostatic direct current fields can be generated, for example, by electrical conductors or magnetoresistors, to which a direct current is applied.

The means for generating an electrostatic direct current field can be designed and arranged in such a way that the blood to be treated can be exposed to the electrostatic direct current field when the blood to be treated passes through the dialyzer and/or while it is in contact with a semipermeable membrane of the dialyzer. To this end, the means for generating an electrostatic direct current field can be arranged in such a way that a part, a predominant part or the entire dialyzer is directly exposed to the electrostatic direct current field along the axis of the direction of flow of the blood to be treated. In particular, the means for generating the electrostatic direct current field can be arranged on the outer surface of the dialyzer of the dialysis device according to the invention or form an integral part of the dialyzer. The means for generating a high-frequency electromagnetic field and the means for generating an electrostatic direct current field are preferably arranged in such a way that the high-frequency electromagnetic field and the electrostatic direct current field overlap wholly or partially. Alternatively, the means for generating a high-frequency electromagnetic field and the means for generating an electrostatic direct current field can be arranged in such a way that the electrostatic direct current field is located downstream of the high-frequency electromagnetic field in the direction of flow of the blood to be treated. In particular, the means for generating the electrostatic direct current field can be designed and arranged in such a way that the electrostatic direct current field is aligned so that it is not substantially parallel to the direction that the blood to be treated flows through the dialyzer. The means for generating the electrostatic direct current field are preferably arranged in the dialyzer in such a way that positively or negatively charged uremic toxins in the blood to be treated are circulated by the electrostatic direct current field in the direction of the dialysis membrane of the dialyzer.

The means for generating an electrostatic direct current field can be arranged in the dialysis device in such a way that the blood to be treated is exposed to the electrostatic direct current field during the entire passage through the dialyzer or only during part of said passage. It is also possible for the means for generating an electrostatic direct current field to be arranged in the dialysis device in such a way that the blood to be treated is exposed to an electrostatic direct current field at several points of its passage through the dialyzer. In a preferred variant the means for generating an electrostatic direct current field are arranged in such a way that the blood to be treated is exposed to the electrostatic direct current field as soon as it enters the dialyzer and substantially during its entire passage through the dialyzer. This approach has the advantage that the elimination of positively or negatively charged uremic toxins released from the protein-bound state can essentially take place along the entire length of the dialyzer and therefore the entire capacity of the dialyzer is available for the exchange of substances with the dialysate.

To achieve the most effective elimination possible of charged uremic toxins released from the protein-bound state, it can be advantageous to arrange means in the dialysis device according to the invention, which generate electrostatic direct current fields with a given electric field strength. Therefore, means are preferably used for generating an electrostatic direct current field, which has an electric field strength of ≤5000 V/m, in particular of ≤1500 V/m, preferably from 0.1 to 1500 V/m, particularly preferably from 1 to 1000 V/m. In a particular embodiment of the dialysis device according to the invention, means are used in order to generate an electrostatic direct current field which has an electric field strength of approx. 250 V/m.

Means and methods for generating suitable electrostatic direct current fields are known to the person skilled in the art such as, for example, suitable field generators. To generate an electrostatic direct current field, the dialysis device according to the invention can, for example, comprise at least two electrical conductors or magnetoresistors, between which the electrostatic direct current field is generated, wherein the at least two electrical conductors or magnetoresistors are arranged on opposite sides of the dialyzer. The means for generating an electrostatic direct current field can also comprise more than two electrical conductors located opposite one another, wherein the electrical conductors are preferably arranged about the dialyzer in such a way that the electrostatic direct current field can be rotated about the axis along the direction of flow of the blood to be treated through the dialyzer. In this case, the electrostatic direct current field can not only be operated statically, but also in a rotating manner if necessary. The rotation speed thus selected is slower than the frequency of the high-frequency electromagnetic field. The rotation of the electrostatic direct current field preferably has a frequency of 100 kHz to 100 MHz, particularly preferably a frequency from 0.5 MHz to 50 MHz, very particularly preferably from 1 MHz to 25 MHz and particularly preferably from 1 MHz to 6 MHz and/or 9 MHz to 13 MHz.

Alternatively, the rotation of the electrostatic direct current field can be modulated with a frequency from 1 Hz to 100 kHz, particularly preferably from 20 Hz to 65 kHz. The rotation of the electrostatic direct current field can particularly preferably be modulated with a frequency of 1 kHz to 100 kHz, very particularly preferably from 20 kHz to 65 kHz. In a particular embodiment of the dialysis device according to the invention, the rotation of the electrostatic direct current field can be modulated with a frequency of 1 Hz to 100 Hz, preferably from 20 Hz to 65 Hz. The rotation of the electrostatic direct current field can prevent a static Helmholtz double layer being built up.

The dialysis device according to the invention can, in addition, comprise a regulating and/or control unit. This regulating and/or control unit can be designed in such a way that it serves to regulate and/or control parameters of the electrostatic direct current field and/or of the high-frequency electromagnetic field. Such parameters can include, for example, the frequency, the field strength, the magnetic flux density and/or the duration of the field. To this end, the regulating and/or control unit can comprise an input unit, a computing unit and, if appropriate, a memory unit, by means of which a user of the dialysis device can regulate and/or control the parameters of the field in question. In a preferred embodiment, the regulating and/or control unit is designed in such a way that a user can also use it to regulate and/or control parameters of the dialysis circuit and/or the blood circuit, such as the flow rate of the blood to be treated and/or the dialyzing fluid and/or the dialysate.

The invention will now be explained in more detail with reference to embodiment examples.

FIGURES

FIG. 1 shows a schematic view of a dialysis device according to the invention.

FIG. 2 shows the amount of uremic toxins (rel. peak areas) in the filtrate in the presence and absence of a high-frequency (HF) field (OH-HPA=p-hydroxyhippuric acid; PAA=phenylacetic acid; IDS=indoxyl sulfate).

EXAMPLES

Example 1: Description of a Dialysis Device According to the Invention

Figure 1:
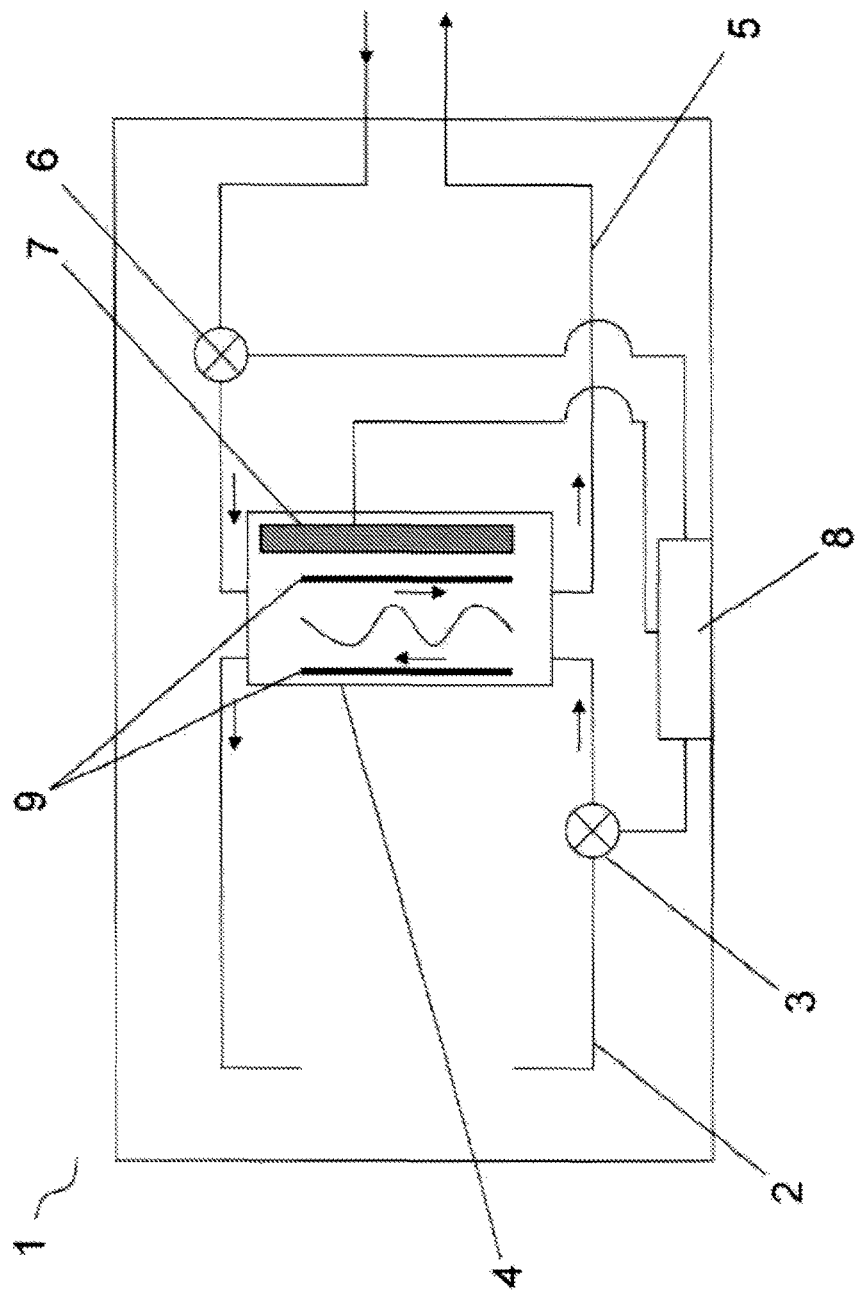

FIG. 1 shows a schematic view of a dialysis device 1 according to the invention, which is suitable for carrying out the use according to the invention. The dialysis device 1 comprises a dialysis circuit 2, a blood circuit 5 and a dialyzer 4, which are interconnected in such a way that blood which circulates in the blood circuit 5 and is to be treated in the dialyzer 4, and dialysate which circulates in the dialysis circuit 2 can be passed next to each other in opposite directions on different sides of the semipermeable membrane, so that an exchange of substances between the blood and the dialysate is possible through the semipermeable membrane of the dialyzer 4. A pump 6 can be provided to transport blood through the blood circuit 5 in a defined direction. A dialysate pump 3 can be provided to transport dialysate through the dialysis circuit in a defined direction. The dialyzer 4 can, for example, be designed as a capillary dialyzer comprising a semipermeable membrane whose size exclusion limit ranges from 10,000 Da to 20,000 Da. In general, the dialysis device 1 according to the invention can be assembled using known, conventional dialysis technology, wherein it can be substantially based on all known dialysis devices or dialysis machines. In addition, the dialyzer 4 comprises means 7 for generating a high-frequency electromagnetic field and means 9 for generating an electrostatic direct current field. Such means 7 can, for example, be a high-frequency coil, a high-frequency electrode and/or a high-frequency capacitor. The means 9 can, for example, be designed as electrical conductors or magnetoresistors which are arranged on opposite sides of the dialyzer 4, so that the dialysis membrane of the dialyzer 4 is located between the two conductors or resistors. The dialysis device 1 according to the invention can, in addition, comprise a regulating and/or control unit 8. This regulating and/or control unit 8 can be designed and connected to the means 7 and/or the means 9 in such a way that it serves to regulate and/or control parameters of the means 7 for generating a high-frequency electromagnetic field and/or 9 means for generating an electrostatic direct current field. Such parameters can include, for example, the electric frequency, the electric field strength, the magnetic flux density and/or the duration of the relevant field. To this end, the regulating and/or control unit 8 can comprise an input unit, a computing unit and a memory unit, by means of which the user of the dialysis device 1 can regulate and/or control the parameters of the high-frequency electromagnetic field and/or parameters of the electrostatic direct current field. In a preferred embodiment, the regulating and/or control unit 8 is designed in such a way that a user can also use it to regulate and/or control parameters of the dialysis circuit 2 and/or the blood circuit 5, such as the flow rates of the blood to be treated and/or of the dialysate.

Example 2 Proof of Effect

The effect of high-frequency electromagnetic fields on the protein-bound portion of uremic toxins was studied by means of in vitro test series. For this purpose, a dialysis module was assembled by embedding loops formed of conventional hemofiltration capillaries in a syringe barrel by means of silicone. An aqueous albumin solution containing the uremic toxins phenylacetic acid, p-hydroxyhippuric acid and indoxyl sulfate was introduced into the module in question. A syringe pump was used to filter this solution by means of the dialysis module for 10 minutes. Then, a high-frequency electromagnetic field was induced in the solution using a high-frequency electrode (HF electrode) 11. The electromagnetic field is incremented by means of a high-frequency voltage source over a period of 10 minutes, from 1 to 20 MHz in 1 MHz increments. In the resulting filtrates, the concentrations of the uremic toxins phenylacetic acid, p-hydroxyhippuric acid and indoxyl sulfate, which had previously been added to the artificial plasma, were determined. The effect of the HF field on the bonds between proteins and uremic toxins could be evaluated by comparing the concentrations of the uremic toxins in the resulting filtrates.

Figure 2:
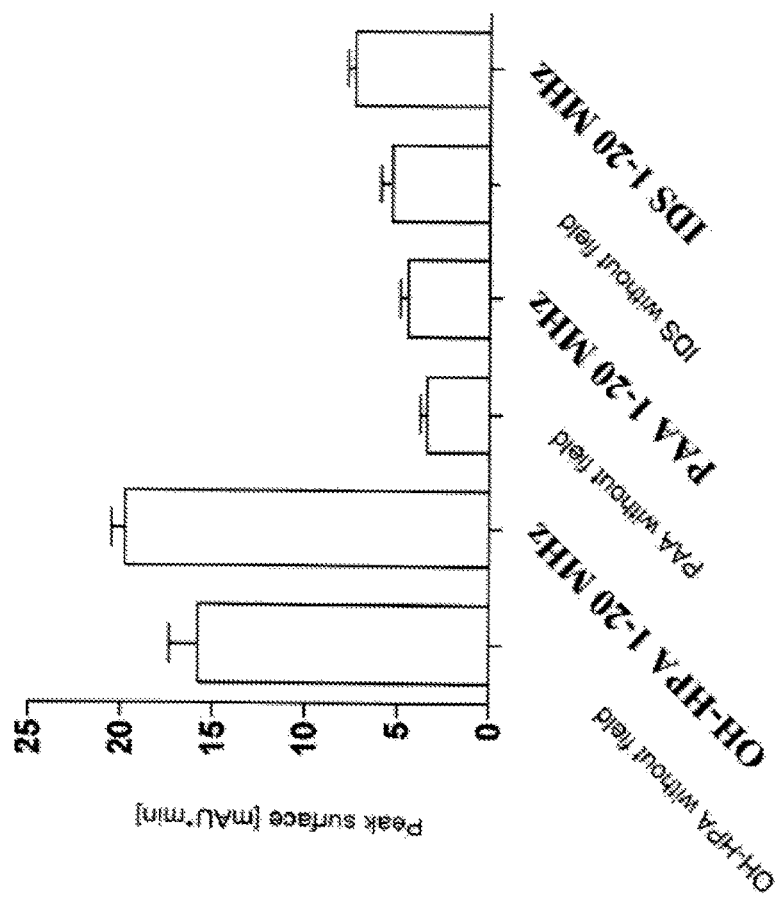
Figure 3:
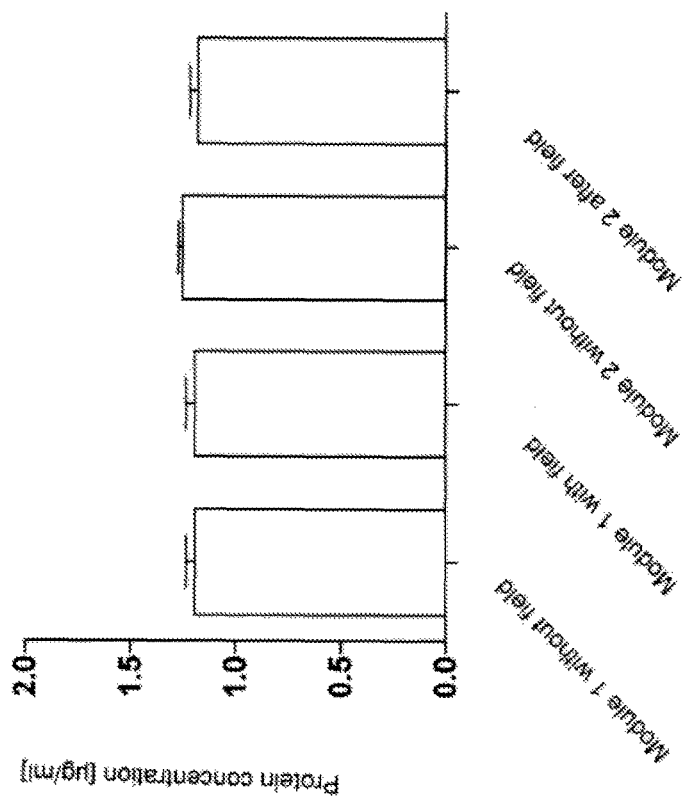
FIG. 3 shows the protein concentrations in the filtrate in the presence and absence of an HF field for two structurally identical modules (no significant difference).

The quantitative determination of the concentrations of the uremic toxins in the resulting filtrates showed that high-frequency electromagnetic fields significantly increase the filtration rates of protein-bound uremic toxins (FIG. 2). To check whether high-frequency electromagnetic fields damage the dialysis membranes, the protein concentration in the filtrate was determined by means of the Bradford protein assay. The results show that no significant changes of the protein concentration can be detected in dialysis modules which are exposed to high-frequency electromagnetic fields, compared to those which are not (FIG. 3). Based on this data macroscopic damage to the membrane can be excluded.

Example 3: Proof of Effect as a Function of the HF Field

Figure 4:
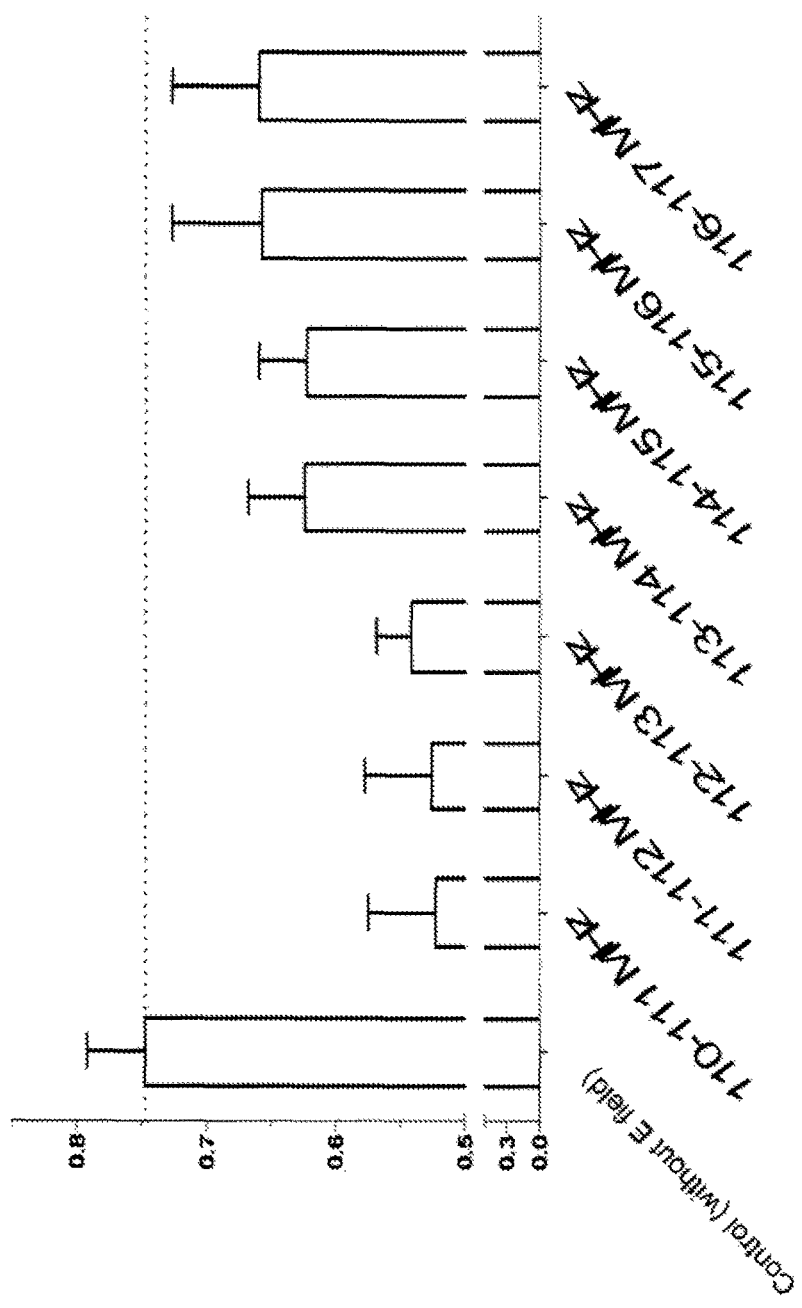
FIG. 4 shows the concentration of phenylacetic acid (PAA) in the retentate as a function of the frequency of the high-frequency electromagnetic (HF) field.

In further studies, it was in particular possible to determine that the frequency range of approximately 110-115 MHz is an effective frequency range for releasing protein-bound uremic toxins. The experimental set-up is similar to that of Example 2, wherein other frequency ranges were used for the high-frequency electromagnetic (HF) field. FIG. 4 shows the effect of the frequencies used on the appropriate release and, subsequently, separation of phenylacetic acid (PAA). No measurable heating of the blood plasma was observed in the experiment. The separation of the protein-bound toxins measured here is therefore not based on a thermal effect.

It has been shown that the frequency ranges indicated summarily below are particularly suitable for separating protein-bound uremic toxins. The relevant frequency ranges are the ranges at which the maximum separation effect was determined. In the frequency ranges which are not indicated, an increased separation was partly determined compared to the control, but this was lower than in the frequency ranges indicated below.

| Suitable frequencies in the HF field (Status as at May 12, 2013) | | | |
| --- | --- | --- | --- |
| Frequencies E field | PAA | IDS | pCRS |
| 80-120 MHz | 110 | 110 | 110 |
| | 110-111 | 110-111 | 110-111 |
| | 111 | 111 | 111 |
| 120-170 MHz | 140-141 | 140-141 | 140-141 |
| | 148-149 | | 151-152 |
| | 160-161 | | |

Example 4: Proof of Effect as a Function of the Frequency of the H Field

Figure 5:
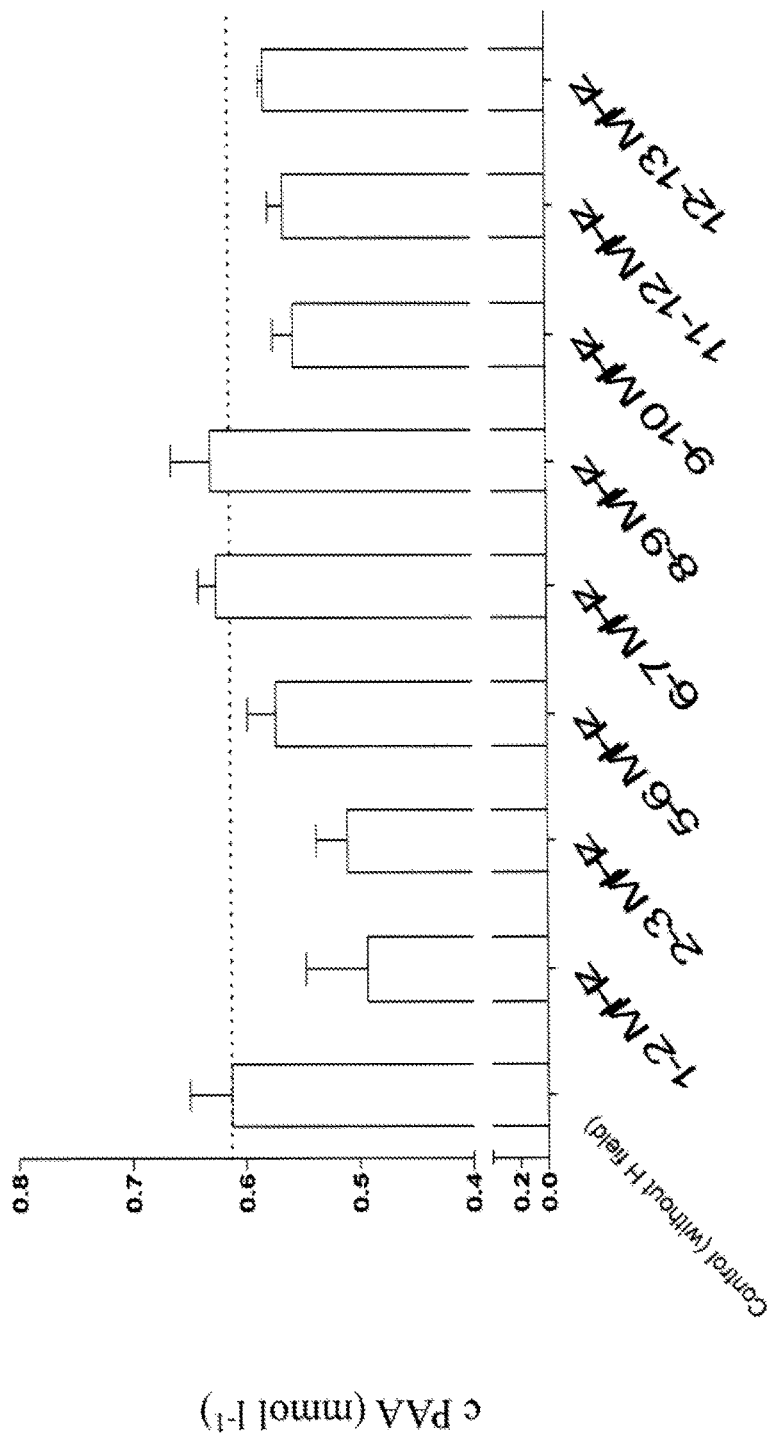
FIG. 5 shows the concentration of phenylacetic acid (PAA) in the retentate as a function of the rotation frequency of the electrostatic (H) field.

The experimental set-up is substantially similar to that of Example 2, wherein instead of the HF field, selected frequency ranges for the electrostatic (H) field were examined. It was thus possible to determine an increased release and, thus, separation of the protein-bound uremic toxins in the range of the H field. It can be inferred from FIG. 5 that the H field range of 1-6 MHz and the range 9-13 MHz is particularly suitable for releasing protein-bound uremic toxins from the protein-bound state and subsequently separating them by means of dialysis (the effect on phenylacetic acid is shown). No measurable heating of the blood plasma was observed in the experiment. The separation of the protein-bound toxins measured here is therefore not based on a thermal effect.

Example 5: Effect of the Field Strength

Figure 6:
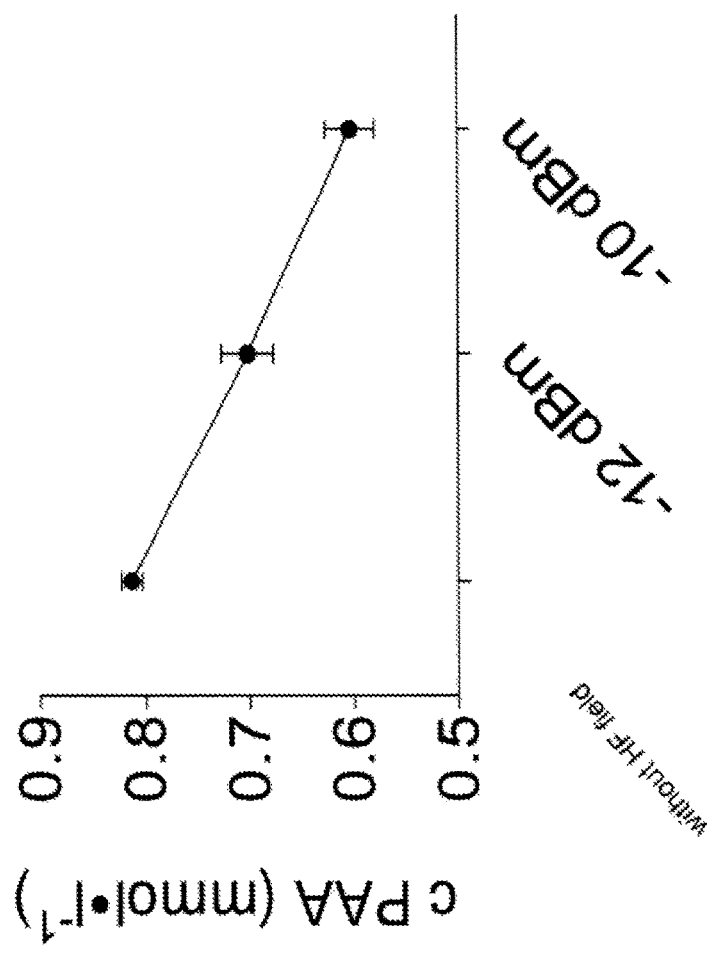
FIG. 6 shows the concentration of phenylacetic acid (PAA) in the retentate as a function of the field strength of a high-frequency electromagnetic (HF) field.

In addition to the frequency of the HF field used, its field strength is also relevant to the resulting release and separation. As the field strength increases, the uremic toxins in question are increasingly released from the protein-bound state and subsequently separated. FIG. 6 shows this effect of an increasing field strength on the content of protein-bound uremic toxins in the retentate, using the example of phenylacetic acid. No measurable heating of the blood plasma was observed in the experiment. The separation of the protein-bound toxins measured here is therefore not based on a thermal effect.

LIST OF REFERENCE NUMERALS

1 Dialysis device
2 Dialysis circuit
3 Dialysate pump
4 Dialyzer
5 Blood circuit
6 Pump
7 Means for generating a high-frequency electromagnetic field
8 Regulating and/or control unit
9 Means for generating an electrostatic direct current field

The invention claimed is:
1. A dialysis device comprising
a dialysis circuit,
a blood circuit; and
a dialyzer,
characterized in that
the dialysis device has means for generating a high-frequency electromagnetic field and means for generating an electrostatic direct current field, wherein both means are designed and arranged in such a way that blood to be treated can be exposed to the high-frequency electromagnetic field and the electrostatic direct current field when passing through the dialyzer,
wherein the means for generating an electrostatic direct current field have at least two electrical conductors, between which the electrostatic direct current field is generated, wherein the two electrical conductors are arranged on opposite sides of the dialyzer, and
wherein the means for generating an electrostatic direct current field have more than two electrical conductors arranged on opposite sides of the dialyzer, wherein the electrical conductors are arranged about the dialyzer in such a way that the electrostatic direct current field can be rotated about the axis along the direction that the blood to be treated flows through the dialyzer.
2. The dialysis device according to claim 1, wherein the means for generating a high-frequency electromagnetic field and the means for generating an electrostatic direct current field are arranged in such a way that the high-frequency electromagnetic field and the electrostatic direct current field overlap wholly or partially.
3. The dialysis device according to claim 1, wherein the means for generating a high-frequency electromagnetic field and the means for generating an electrostatic direct current field are arranged in such a way that the electrostatic direct current field is located downstream of the high-frequency electromagnetic field in the direction of flow of the blood to be treated.
4. The dialysis device according to claim 1, wherein the means for generating the electrostatic direct current field are designed and arranged in such a way that the electrostatic direct current field is not aligned substantially parallel to the direction that the blood to be treated flows through the dialyzer.
5. The dialysis device according to claim 1, wherein the rotation of the electrostatic direct current field can be modulated with a frequency from 100 kHz to 100 MHz.
6. The dialysis device according to claim 1, wherein the electric field strength of the electrostatic direct current field is ≤5000 V/m.

7. The dialysis device according to claim 1, wherein the means for generating a high-frequency electromagnetic field comprise at least one of a high-frequency coil, a high-frequency electrode, and a high-frequency capacitor.

8. The dialysis device according to claim 1, wherein the dialysis device comprises at least one of a regulating unit and control unit, by means of which parameters of the electrostatic direct current field can be regulated or controlled.

9. The dialysis device according to claim 1, wherein the dialysis device is designed in such a way that the blood to be treated can be exposed to the high-frequency electromagnetic field during its entire passage through the dialyzer or during part of said passage.

10. The dialysis device according to claim 1, wherein the dialysis device is designed in such a way that the blood to be treated can be exposed to the electrostatic direct current field during its entire passage through the dialyzer or during part of said passage.

11. The dialysis device according to claim 1, wherein the means for generating a high-frequency electromagnetic field are designed with a frequency from 10 MHz to 500 MHz.

12. The dialysis device according to claim 1, wherein the means for generating a high-frequency electromagnetic field are designed with an electric field strength of 1 to 250 V/m.

13. The dialysis device according to claim 1, wherein at least one of the means for generating a high-frequency electromagnetic field and the means for generating an electrostatic direct current field are an integral part of the dialyzer.

14. The dialysis device according to claim 1, wherein the rotation of the electrostatic direct current field can be modulated with a frequency from 0.5 MHz to 50 MHz.

15. The dialysis device according to claim 1, wherein the rotation of the electrostatic direct current field can be modulated with a frequency from 1 MHz to 25 MHz.

16. The dialysis device according to claim 1, wherein the means for generating a high-frequency electromagnetic field are designed with a frequency from 80 MHz to 170 MHz.

17. The dialysis device according to claim 1, wherein the means for generating a high-frequency electromagnetic field are designed with a frequency from 100 MHz to 120 MHz.

* * * * *